United States Patent [19]

Campbell et al.

[11] 4,328,594

[45] May 11, 1982

[54] PROSTHETIC FOOT

[76] Inventors: John W. Campbell, 2599 Rosewood St.; Charles W. Childs, 2880 David La., both of Medford, Oreg. 97501

[21] Appl. No.: 121,216

[22] Filed: Feb. 13, 1980

[51] Int. Cl.³ .............................................. A61F 1/08
[52] U.S. Cl. ................................................ 3/7; 3/6.1
[58] Field of Search ............................ 3/2, 6, 6.1, 7, 8

[56] References Cited

U.S. PATENT DOCUMENTS

| | | | |
|---|---|---|---|
| 43,031 | 6/1864 | Kirchmann . | |
| 456,206 | 7/1891 | Rowley | 3/7 |
| 457,823 | 8/1891 | Rounds | 3/6.1 X |
| 961,582 | 6/1910 | Bradley et al. . | |
| 1,219,374 | 3/1917 | Carrico | 3/7 |
| 1,294,632 | 2/1919 | Dickson . | |
| 2,453,969 | 11/1948 | Carter | 3/2 |
| 2,556,525 | 6/1951 | Drennon | 3/6 |
| 3,098,239 | 7/1963 | Nader | 3/7 |
| 3,484,871 | 12/1969 | Orange | 3/7 |
| 3,833,941 | 9/1974 | Wagner | 3/7 |
| 4,091,472 | 5/1978 | Daker et al. | 3/7 |
| 4,177,525 | 12/1979 | Arbogast et al. | 3/7 |

FOREIGN PATENT DOCUMENTS

| | | | |
|---|---|---|---|
| 811714 | 8/1951 | Fed. Rep. of Germany | 3/7 |
| 1371996 | 10/1974 | United Kingdom | 3/7 |

OTHER PUBLICATIONS

"Course for Prosthetists in Above-Knee Prosthesis Fitting and Alignment", Anderson, et al, Mar. 1, 1956, U. of Calif. L. A., School of Medicine, pp. 244-250.
*Orthopaedic Appliance Atlas*, vol. 2, "Artificial Limbs", 1960, USA, Edwards Bros, Inc., Ann. Arbor, Mich., pp. 148-161.
*Human Limbs and Their Substitutes*, Klopsteg, et al., Hafner Publishing Co., New York, 1954, 31 E. 10th St., New York, N.Y. 10003, pp. 487-515.
*Prosthetics and Orthotics International*, Dec. 1978, vol. 2, No. 3, Printed by David J. Clark, Limited, Glasgow, Scotland, pp. 125-136.
*Development of an Epoxy Foot Mold and a Lightweight Foam Artificial Foot*, 1968, Navy Prosthetic Research Lab., Naval Hosp., Oakland, Calif., pp. a-x.

*Primary Examiner*—Clifford D. Crowder
*Attorney, Agent, or Firm*—Klarquist, Sparkman, Campbell, Leigh, Whinston & Dellett

[57] ABSTRACT

A prosthetic foot includes an elongated one-piece semi-rigid keel having a half dome-shaped arch and a thinned toe break region. A rigid bolt block, with a lower portion of reduced size to accommodate a cushioned heel, is fastened to the posterior end of the keel. To rigidify the foot during toe-off, a first substantially inelastic strap is provided. This first strap is fastened at one end to the bolt block, extends across a lower region of the arch, and is fastened at its opposite end to the keel forwardly of the toe break region. A second substantially inelastic strap is positioned above the first strap and is fastened at one end to the bolt block, extends across a mid-portion of the arch, and has its other end fastened to the keel between the arch and toe break region. This second strap rigidifies the foot when in a foot flat position. A flexible foot-shaped cover layer generally envelopes the two straps, keel and bolt block, fills in the toe break region and a large portion of the arch. Also, the cover layer is thickened adjacent to the reduced portion of the heel block to provide a cushioned heel for the foot.

19 Claims, 5 Drawing Figures

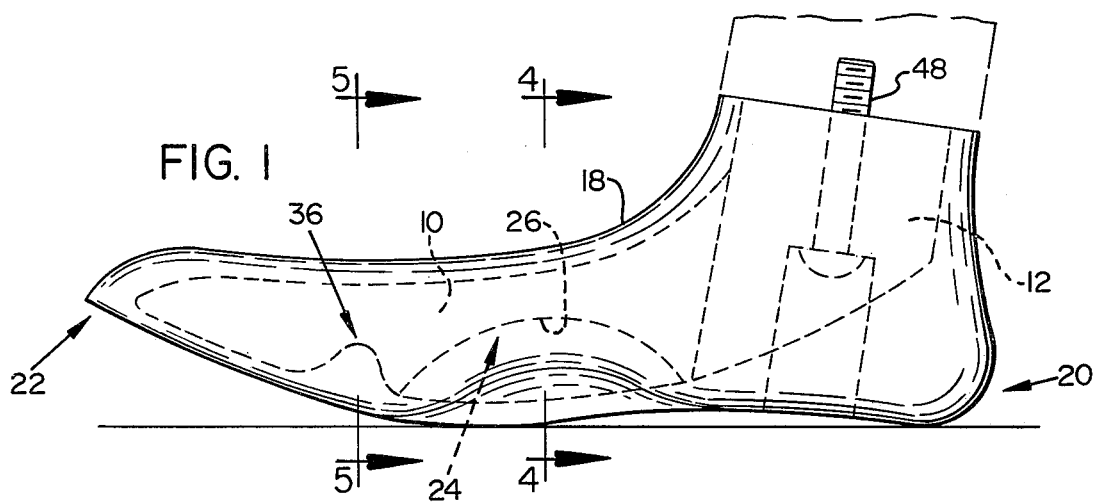
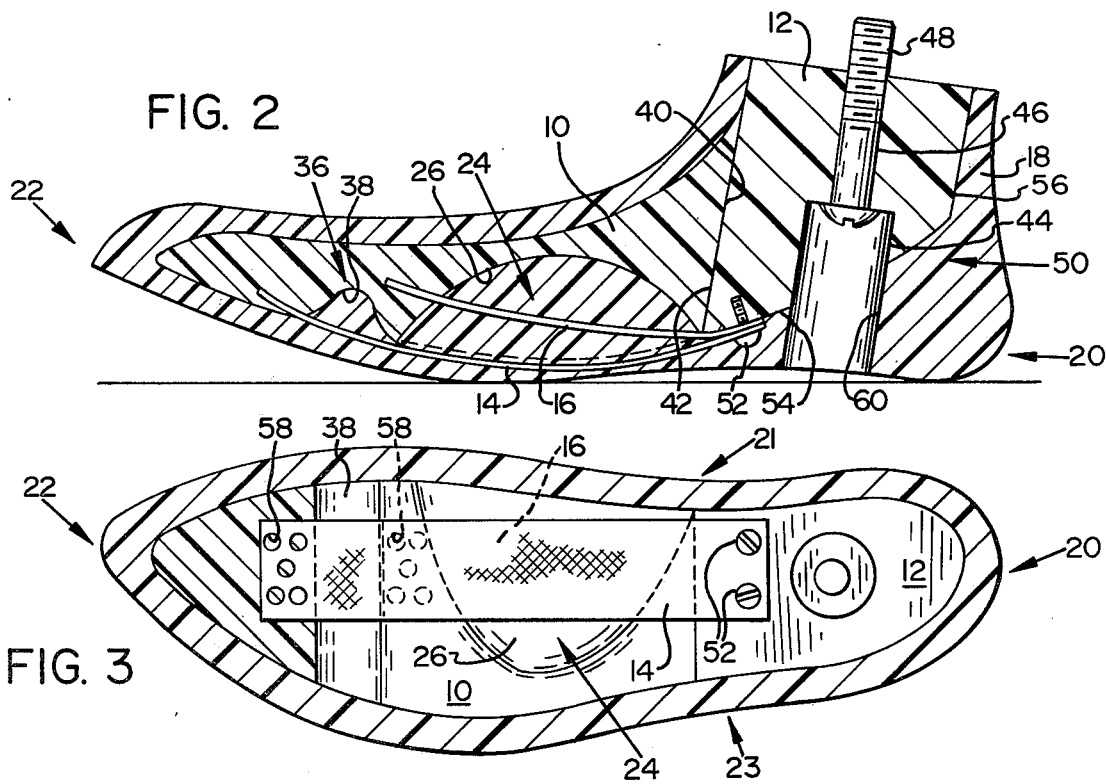
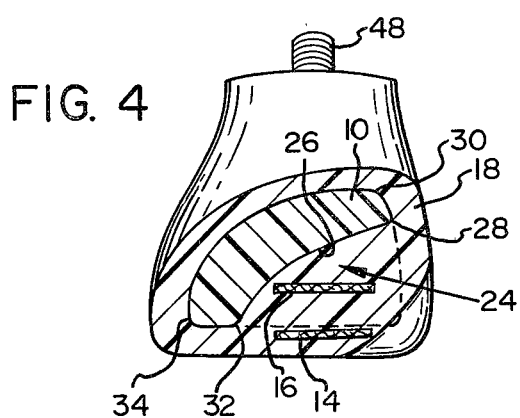
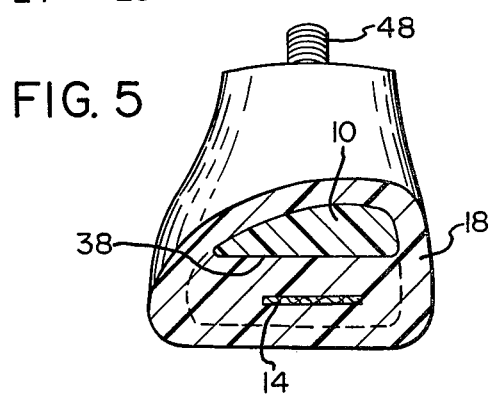

PROSTHETIC FOOT

BACKGROUND OF THE INVENTION

1. Field of the Invention

The present invention relates to prosthetic feet, and more particularly to such feet which lack mechanical joints.

2. Description of the Prior Art

One of the more common prosthetic feet is known as the SACH foot characterized by a rigid keel and bolt block surrounded by a layer of somewhat flexible material. Typically, SACH feet have rigid belting which is fastened to a lower surface of the keel and extends forwardly into the toe region of the foot. Also, the heels of SACH feet are cushioned.

Although SACH feet have some advantages over simple peg legs and other completely rigid feet, they are nevertheless very rigid. Because of this rigidity, SACH feet are virtually incapable of dorsiflexion and plantarflexion, as well as inversion and eversion. Consequently, these feet inhibit walking by a user. Also, these feet lack the ability to conform to uneven surfaces so that they are difficult to use under these conditions. Furthermore, the SACH foot, in the absence of a mechanical ankle joint, does not permit transverse rotation of the foot, that is rotation in a horizontal plane, relative to the long axis of the attached leg. For this reason, users of these feet often have an abnormal gait.

U.S. Pat. Nos. 3,098,239, 3,484,871 and 3,833,941 are illustrative of typical SACH feet.

Solid rubber feet have also been employed, but these typically are very heavy and stiff. The excess weight of such feet increases the energy required of a user during walking. That is, during walking a human foot acts like a pendulum that must be accelerated when the swing of the leg is started and decelerated when the heel hits the ground. The energy required to accelerate and decelerate the leg is related to the center of mass of the leg and increases as this center is shifted distally, such as when weight is added to the foot. As an added drawback, amputees typically have fewer muscles to accomplish acceleration and deceleration of the leg so that excess weight of rubber feet is particularly troublesome. Also, the stiffness of such feet inhibits their motion during walking in much the same manner as SACH feet.

In an attempt to provide greater flexibility, simple inflated feet have been employed. Also, feet combining rigid blocks and sponge and vulcanized rubber inserts, the combinations joined together by rayon reinforcing and binding cord have also been employed. One such foot is known as the Jaipur foot and was developed in India. Although such feet are usually flexible enough to conform to uneven ground, they suffer from the disadvantage of being too flexible during use. This is particularly true during toe-off, when in the course of walking a user's weight is shifted forwardly to the toe region of the foot just prior to picking the foot off the ground. That is, this flexibility inhibits the user's ability to thrust forwardly off the toes.

Still other forms of prior art feet have attempted to provide mobility through the use of mechanical joints. However, such joints tend to fail as a result of the continuously and repetitively applied stresses during use. Furthermore, in many of these types of feet, the joints are exposed where they can trap dirt, grit, and other abrasive and corrosive materials. This contributes to their more rapid failure. Furthermore, feet with mechanical joints are typically more difficult and costly to manufacture. In addition, mechanical joints tend to add weight to the foot which, as explained above, increases the energy required by a user during walking. U.S. Pat. No. 2,556,525 is exemplary of such devices and includes an elongated keel of a relatively stiffened material, for example, vulcanized rubber, surrounded by a soft sponge rubber material with a steel anchor plate embedded in the foot to provide a lower anchor for springs used in an ankle joint. Other examples of such devices are disclosed in U.S. Pat. Nos. 43,031, 961,582, 1,294,632 and 2,453,969.

Therefore, a need exists for a prosthetic foot which, without mechanical joints, is sufficiently rigid and yet is capable of desirable movement during walking.

SUMMARY OF THE INVENTION

The overall invention relates to a prosthetic foot with an elongated semi-rigid keel having a raised, preferably half domed-shaped arch. A thinned toe break region extends laterally across the keel and the keel is fastened to a rigid bolt block to form a keel-bolt block assembly. A first connector is fastened at one end to the keel-bolt block assembly rearwardly of the arch, spans a lower region of the arch, and is connected at its other end forwardly of the arch to rigidify the foot during toe-off. A second connector is also fastened to the bolt block assembly rearwardly of the arch, spans a midsection of the arch, and is connected at its other end ahead of the arch for rigidifying the arch primarily when the foot is in its foot flat position. A flexible foot-shaped covering layer envelopes the keel, bolt block, and connectors to complete the foot.

As an additional feature of the invention, the forward end of the first connector is fastened to the keel ahead of the toe break region to rigidify the toe section of the foot during toe-off.

As still another feature of the invention, the second connector is fastened to the keel at its anterior end between the arch and toe break region.

As a more specific feature of the invention, the first and second connectors comprise substantially inelastic straps.

As a still more specific feature of the invention, the straps are under approximately twelve pounds tension when the foot is in a foot flat position without an applied load.

As a secondary and optional feature of the invention, the straps are slidable relative to the covering layer.

In addition to the overall prosthetic foot, the present invention also relates to a semi-rigid keel as described above both with and without a toe break region.

Furthermore, the invention relates to a prosthetic foot having a semi-rigid elongated keel with a raised arch in combination with connectors as described above.

It is an overall object of the invention to provide an improved prosthetic foot.

It is another object of the invention to provide a prosthetic foot which closely mimics the motion of a natural foot.

It is still another object of the present invention to provide a prosthetic foot which is flexible when planted and converts to a semi-rigid lever during toe-off.

Still another object of the invention is to provide a prosthetic foot which is capable of simulating plantarflexion, dorsiflexion, inversion, eversion and transverse rotation about the long axis of the attached leg.

It is a further object of the invention to provide a prosthetic foot capable of conforming to uneven ground.

A further object of the invention is to provide a prosthetic foot capable of mimicing the motion of a natural foot without the need for mechanical joints, and which is lighter than mechanically jointed feet capable of similar motion.

An additional object of the invention is to provide a prosthetic foot which is relatively easy and inexpensive to manufacture.

Another object of the invention is to provide a prosthetic foot which is durable and resistant to adverse environmental conditions such as moisture.

The foregoing and other objects, features and advantages of the present invention will become more apparent from the following detailed description which proceeds with reference to the accompanying drawing.

BRIEF DESCRIPTION OF THE DRAWING

In the drawing:

FIG. 1 is a side elevational view of the medial side of a foot in acordance with the invention with the keel portion and bolt block portion thereof shown in dashed lines;

FIG. 2 is a longitudinal sectional view of the foot of FIG. 1;

FIG. 3 is a bottom plan view of the prosthetic foot of FIG. 1, partially in section and with a portion of the outer cover layer removed;

FIG. 4 is a cross sectional view of the foot of FIG. 1, taken along lines 4—4 thereof; and FIG. 5 is a cross sectional view of the foot of FIG. 1, taken along lines 5—5 thereof.

DETAILED DESCRIPTION OF A PREFERRED EMBODIMENT

With reference to the figures, a prosthetic foot in accordance with the invention includes an elongated one-piece semi-rigid keel 10, a bolt block 12, plural connector means such as straps 14, 16 and an outer covering layer 18 generally enveloping the keel, bolt block and straps.

For reference purposes, the posterior or rear end of the foot is designated 20 and the anterior or forward end of the foot is designated 22. In addition, the medial side of the foot is designated 21 and the lateral side 23. Keel 10 has a raised arch 24 which is preferably in the shape of half of a dome. More specifically, the illustrated arch 24 is defined by an undersurface 26 of the keel such that a cross section of the arch taken in a plane through its broadest portion, as shown in FIG. 4, is generally in the shape of one-fourth of an ellipse. In this preferred embodiment of the arch, each cross section of the arch taken in a plane from the lateral side of the foot to the medial side of the foot is also in the shape of approximately one-fourth of an ellipse. Although the dimensions are varied depending on the size of the prosthetic foot being constructed, with reference to FIG. 4, the distance from the apex 28 of the arch 24 to the top of the keel instep 30 is approximately seven-eighths of an inch. In addition, the lower lateral-most portion 32 of the arch 24 is approximately seven-eighths of an inch from the lateral border 34 of the keel.

The keel is of a resilient material. The keel is preferably constructed of a semi-rigid polymer material in the range of sixty-five to seventy-five Durameter on the Shore A scale. As a specific example, a polyurethane elastomer may be employed and may include a filler of glass bubbles or micro balloons of up to fifteen percent by weight. One suitable urethane material for the keel is Calthane 1900 produced by Cal Polymers, Inc. of 2115 Gaylord St., Long Beach, Calif., and is typically used in making flexible molds.

A toe break region 36 is also provided in keel 10 to enhance flexibility of the keel forwardly of the toe break relative to the keel rearwardly of the toe break. Although other toe breaks are suitable, the illustrated toe break extends laterally across the keel from its medial side to its lateral side. The keel 10 is thinned, that is not as thick in the vertical direction, to provide the toe break. As best seen in FIG. 2, the undersurface 38 of keel 10 is arched to define the toe break region forwardly of arch 24.

Keel 10 has a planar posterior attachment surface 40 for connection to a corresponding surface 42 at the forward side of bolt block 12 to form a keel-bolt block assembly. Keel 10 is formed in a suitable manner, as by injecting a polyurethane elastomer into a mold and allowing it to cure. With this manufacturing technique, the bolt block 12 may be inserted into the mold prior to injection of the elastomer so that as the elastomer of keel 10 cures, it bonds to the bolt block. Of course, keel 10 may be manufactured separately and fastened to the bolt block in any suitable manner. As previously mentioned, bolt block 12 is preferably of a rigid material such as, for example, syntactic or phenolic resin, or rigid foam of four to eight pounds density or better. A first hole 44 is bored upwardly from the bottom of the bolt block and partially through it. In addition, a second bore 46, concentric with first bore 44 and of a smaller diameter than the first bore, extends from the first bore through the upper surface of the bolt block. Hole 46 accommodates the shank of a leg attachment bolt 48 while hole 44 accommodates the head of this bolt. Also, the lower rear portion 50 of bolt block 12 is of reduced size for purposes explained below.

Strap 14 is secured at its posterior end to the keel-bolt block assembly posteriorly of arch 24, extends across a lower region of the arch, and is fastened at its anterior end to keel 10 forwardly of arch 24. Strap 16 is similarly fastened at its posterior end to the keel-bolt block assembly rearwardly of the arch, extends across the midsection of the arch, and is fastened at its anterior end to the keel forwardly of the arch. In the preferred embodiment, as can be seen in FIGS. 2 and 3, straps 14 and 16 are secured by screws 52 to a lower surface 54 of bolt block 12. Alternately, these straps may be secured to the rear surface 56 of the bolt block, in which case less strain is placed on the straps point of connection between the straps and screws during use of the foot. Also, in the preferred embodiment, the anterior end of strap 14 is fastened to the keel forwardly of toe break 38 and the anterior end of strap 16 is fastened to the keel generally between the toe break 38 and arch 24. These straps may be secured to the keel in any suitable manner and, as illustrated in FIGS. 2 and 3, may be embedded in the keel as the keel material cures. Holes 58 are provided in the embedded end portions of straps 14, 16 and are filled with the keel material so that as this material cures it securely fastens the straps in place.

Preferably, straps 14, 16 are of a relatively inelastic material such as dacron webbing, one and one-half inches wide. Furthermore, during manufacture of the foot, tension is applied to these straps prior to securing them in place with screws 52. It has been found that by placing these straps under approximately twelve pounds tension when the foot is in its foot flat position without an applied load, as shown in FIG. 2, the straps function to rigidify the keel during walking.

Cover layer 18, as mentioned above, generally envelopes or surrounds keel 10, straps 14, 16 and bolt block 12. However, typically the upper surface of the bolt block 12 is not coated with the covering material as it is desirable that this surface be attached directly to the leg.

As can be seen in FIG. 2, cover layer 18 fills the toe break region 38 and substantially fills arch 24. Typically, a sufficient arch is left in the covering material so that the foot will fit in a normal shoe. Also, the cover layer is thickened in the area of the reduced portion 50 of bolt block 12 to provide a cushioned heel for the foot. A circular bore 60 communicates from bore 44 through the cover layer to the lower surface of the foot and provides an access passageway for bolt 48 in the event removal of the bolt and foot is desired.

Although a number of suitable materials may be used for cover layer 18, preferably it comprises a self-skinning flexible, high modulus, medium density flexible foam material. In such materials, skin thickness is typically controlled by temperature and packing of the mold. The skin of such materials is generally quite durable. One suitable material is designated Foamex DS 218 and produced by Foamex Company of 1641 Border Ave., Torrence, Calif.

An an optional feature, straps 14, 16 are coated with a mold release material prior to the formation of the cover layer so that after cover layer 18 is formed, the straps 14, 16 are free to slide relative to the cover layer.

With this construction, the foot of the present invention is most flexible as the heel is first planted. Thereafter, when the foot is moved to the foot flat position, as shown in FIG. 2, strap 16 rigidifies the arch to stabilize the foot in this position. In effect, strap 16 and the keel defining the arch act as a truss providing rigidity to the arch as weight is applied, primarily when the foot is in the foot flat position.

As weight is shifted downwardly during walking, strap 14 tightens. This rigidifies the foot and the foot becomes more rigid as the weight forward shifting of the weight continues. In effect, strap 14 cooperates with the keel to provide a rigid lever from bolt block 12 to the forwardmost portion of the keel. As the foot approaches toe-off, strap 14 rigidifies the keel forwardly of the toe break so that the user can thrust forwardly off the toe portion of the foot. Thus, when at toe-off, strap 14 effectively makes the keel a rigid lever from the bolt block 12 forwardly to the toe portion and thereby provides a more efficient foot for the user.

At the same time, the construction permits inversion, eversion, and transverse rotation of the foot as well as dorsiflexion and plantarflexion so that the prosthetic foot closely mimics the motion of a natural foot.

Having illustrated and described the principles of our invention with reference to one preferred embodiment, it should be apparent to those skilled in the art that this invention can be modified in arrangement and detail without departing from such principles.

We claim:

1. An elongated resilient keel for a prosthetic foot, said keel having a half dome shaped arch; said keel also having a bolt block attachment surface posteriorly of said arch and a thinned toe break region extending laterally across the keel and positioned anteriorly of said arch.

2. A keel according to claim 1 in which the cross section of the arch in a plane from the lateral side of the keel to the medial side of the keel through the broadest portion is generally in the shape of one-fourth an ellipse.

3. A keel according to claim 2 having a keel instep and a lateral border and in which the apex of the arch is approximately seven-eighths of an inch from the top of the keel instep and the lateral most portion of the arch is approximately seven-eighths of an inch from the lateral border of the keel.

4. A keel according to claim 1 in which each cross section of the arch taken in a plane from the lateral side of the keel to the medial side of the keel is generally in the shape of one-fourth of an ellipse.

5. A keel according to claim 1 of a polymer material generally in the range of sixty-five to seventy-five Durameter on the Shore A scale.

6. A keel according to claim 5 of a polyurethane elastomer material.

7. A prosthetic foot comprising:
an elongated resilient keel having a raised arch; and
first connector means extending longitudinally along the keel across a lower portion of the arch and being spaced below a central portion of the arch for rigidifying the keel during toe-off by a user using the foot.

8. A prosthetic foot according to claim 7 in which said first connector means comprises a first substantially inelastic strap.

9. A prosthetic foot comprising:
an elongated resilient keel having a raised arch;
first connector means extending longitudinally along the keel across a lower portion of the arch and being spaced below a central portion of the arch for rigidifying the keel during toe-off by a user using the foot; and
in which said keel includes a toe break region extending laterally across the keel and positioned anteriorly of said arch, said first connector means being fastened at its anterior end to a portion of the keel anteriorly of the toe break region.

10. A prosthetic foot comprising an elongated resilient keel having a raised arch;
first connector means extending longitudinally along the keel across a lower portion of the arch and being spaced below a central portion of the arch for rigidifying the keel during toe-off by a user using the foot; and
including second connector means extending longitudinally along the keel across said arch spaced above said first connector means and being spaced below a central portion of the arch; said second connector means comprising means for stabilizing the foot primarily when the foot is positioned by a user in a foot flat position between initial heel contact of the foot and toe off of the foot.

11. A prosthetic foot according to claim 10 in which said keel includes a half dome-shaped arch.

12. A prosthetic foot according to claim 10 or 11 in which said first connector means comprises a first substantially inelastic strap and in which said second connector means comprises a second substantially inelastic strap.

13. A prosthetic foot according to claim 12 including a bolt block posteriorly of the keel and in which said keel includes a thinned toe break region extending laterally across the keel and positioned anteriorly of said arch, said first and second straps each being attached at their posterior end to said bolt block, said first strap being attached at its anterior end to the keel anteriorly of said toe break region and said second strap being attached at its anterior end to the keel anteriorly of the arch and posteriorly of the toe break region.

14. A prosthetic foot comprising:
an elongated resilient keel having a half dome shaped arch and a toe break region extending laterally across the keel and positioned anteriorly of the arch;
a rigid bolt block fastened to a posterior end portion of the keel to form a keel-bolt block assembly;
a first strap extending longitudinally along the keel and across a lower portion of the arch, said first strap being fastened at its posterior end to the keel-bolt block assembly posteriorly of the arch and fastened at its anterior end to the keel anteriorly of the toe break region;
a second strap extending longitudinally along the keel and across a mid-portion of the arch, said second strap being fastened at its posterior end to the keel-bolt block assembly posteriorly of the arch and at its anterior end to the keel anteriorly of the arch; and
a foot-shaped flexible cover layer generally enveloping the keel-bolt block assembly and first and second straps.

15. A prosthetic foot according to claim 14 in which the lower posterior portion of said bolt block is of a reduced size and said cover layer is thickened in the region of said reduced portion of the bolt block to provide a cushioned heel for the foot.

16. A prosthetic foot according to claim 14 in which the anterior end of said second strap is fastened to said keel between said toe break region and said arch.

17. A prosthetic foot according to claim 14 in which said first and second straps are slidable relative to said cover layer.

18. A prosthetic foot according to claim 17 in which said straps are under approximately twelve pounds tension when the foot is in a foot flat position without an applied load by a user.

19. A prosthetic foot comprising:
an elongated resilient keel having a half dome shaped arch and a thinned toe break region extending laterally across the keel and positioned anteriorly of the arch;
a rigid bolt block fastened to a posterior end surface of the keel to form a keel-bolt block assembly, the lower posterior portion of the bolt block being of a reduced size;
a first substantially inelastic strap extending longitudinally along the keel and across a lower portion of the arch, said first strap being attached at its posterior end portion to the bolt block and at its anterior end portion to the keel anteriorly of the toe break region;
a second substantially inelastic strap extending longitudinally along the keel and across a mid-portion of the arch, said second strap being attached at its posterior end portion to the bolt block and at its anterior end portion to the keel between the arch and toe break region;
said first and second straps being fastened under approximately twelve pounds tension when said foot is in its foot flat position without an applied load;
a foot-shaped flexible cover layer generally enveloping the keel-bolt block assembly and said first and second straps, said cover layer filling in the toe break region of the keel and substantially filling in said arch, said cover layer also being thickened in the region of the reduced portion of the bolt block to provide a cushioned heel for the foot.

* * * * *